United States Patent
Lopez

(10) Patent No.: US 10,913,431 B1
(45) Date of Patent: Feb. 9, 2021

(54) MOVING TUNNEL SANITIZER

(71) Applicant: Javier Lopez, Yorba Linda, CA (US)

(72) Inventor: Javier Lopez, Yorba Linda, CA (US)

(*) Notice: Subject to any disclaimer, the term of this patent is extended or adjusted under 35 U.S.C. 154(b) by 0 days.

(21) Appl. No.: 16/936,185

(22) Filed: Jul. 22, 2020

(51) Int. Cl.
| | | |
|---|---|---|
| *A61L 2/22* | (2006.01) | |
| *A61L 2/10* | (2006.01) | |
| *A61L 2/18* | (2006.01) | |
| *B60S 3/04* | (2006.01) | |
| *B08B 3/02* | (2006.01) | |
| *A47F 10/04* | (2006.01) | |

(52) U.S. Cl.
CPC .............. *B60S 3/04* (2013.01); *A47F 10/04* (2013.01); *A61L 2/18* (2013.01); *B08B 3/022* (2013.01)

(58) Field of Classification Search
CPC .......... A61L 2/22; A61L 2/18; A61L 2202/16; A61L 2/10; B60S 3/04
See application file for complete search history.

(56) References Cited

U.S. PATENT DOCUMENTS

| | | | |
|---|---|---|---|
| 7,258,125 | B2 | 8/2007 | Holbrook |
| 7,380,627 | B2 | 6/2008 | Huang et al. |
| 7,516,967 | B2 | 4/2009 | Schwei et al. |
| 7,791,044 | B1 | 9/2010 | Taylor et al. |
| 9,198,990 | B2 | 12/2015 | Hays et al. |
| 2005/0214159 | A1* | 9/2005 | Schwei ............... A61L 2/24 422/28 |
| 2006/0011220 | A1 | 1/2006 | Mueller |
| 2008/0210268 | A1 | 9/2008 | Metheny et al. |

* cited by examiner

*Primary Examiner* — Kevin Joyner
(74) *Attorney, Agent, or Firm* — Clement Cheng

(57) ABSTRACT

A moving tunnel sanitizer includes a frame forming a tunnel with a tunnel opening through the frame. A right wall supports a right side of the frame. A left wall supports a left side of the frame. A right front wheel and a right rear wheel support the right wall. A left front wheel and a left rear wheel supports the left wall. A top member makes a rigid connection between the right wall to the left wall. Nozzles are mounted on the tunnel on the right wall and on the left wall. A fluid tank stores a sanitizing fluid. The fluid tank is connected to the nozzles by fluid tubing. A left motor and a right motor are drive motors. The left motor drives either the front left wheel or the rear left wheel. The right motor drives the front left wheel or the front right wheel.

8 Claims, 17 Drawing Sheets

MOVING TUNNEL SANITIZER

FIELD OF THE INVENTION

The present invention is in the field of sanitization equipment.

DISCUSSION OF RELATED ART

COVID 19 has presented a wide variety of challenges for the world economy. Current sanitation equipment needs to be improved in design for addressing new prolific coronaviruses such as COVID 19. One key element of combating new prolific coronaviruses is through automatic sanitation equipment. What is needed is automatic sanitation equipment for improving anti-virus response.

A wide variety of different sanitizers have been marshaled for the war against viruses. For example, in U.S. Pat. No. 7,380,627, Remote control vehicle with UV sterilizer by inventor Chih-Hong Huang et al., published Jun. 3, 2008 the abstract discloses, "A remote control vehicle includes a cart, an ultraviolet radiation tube and a remote control device. The cart has a video device, a control signal antenna and a video signal antenna. The control signal antenna and the video signal antenna are disposed by the video device. The remote control device is used to send out control signals to the control signal antenna so as to control the motions of the cart. In use, users place the cart in an air conduit of an air conditioning system and steer it with the remote control device so that the cart may reach every part in the air conduit. Also, the ultraviolet radiation tube is activated to kill all the bacteria and microorganisms in the air conduits. Such that, the users will not be exposed to the ultraviolet radiation emitted by the tube, and hence the safety of use is assured."

For example, in U.S. Pat. No. 7,791,044B1, Station for disinfecting publicly-used equipment by inventor Thomas L. Taylor et al., published Sep. 7, 2010 the abstract discloses, "A device for disinfecting publicly-used equipment includes a plurality of reflective units disposed along the interior of each wall of the device. Each of the reflective units can include a reflective back section and at least three reflective sections disposed about the reflective back section. UV lamps can be disposed to extend along the walls, and at partially disposed adjacent to a one or more reflective back sections of the reflective units. The UV lamps together with the reflective units collectively direct sufficient UV light on the equipment such that the equipment can be disinfected. The walls and ceiling of the device define a tunnel into which the equipment to be disinfected is inserted. Optionally, the device can include a door to prevent children and others from entering the tunnel while the UV lamps are illuminated."

For example, in U.S. Pat. No. 9,198,990B2, Station Disinfecting device by inventor Richard Glen Fletcher published Dec. 1, 2015 the abstract discloses, "A sanitizing system uses ultraviolet light within a housing having an interior chamber. When items such as shopping carts or wheel chairs are moved into and out of the interior chamber, a cover is moved to reduce the light shining out of the housing. The cover is coordinated with the door of the housing to limit light shining on the users of the system. In another configuration, a switch is used to turn off the light source to reduce the light shining out of the housing when items such as shopping carts or wheel chairs are moved into and out of the interior chamber. In both of the systems described above, the sanitizing system may use a single sanitizing source such as a UV light source or a combination of sanitizing systems such as a UV light source in combination with a source of disinfecting plasma."

For example, in U.S. Pat. No. 7,258,125B2, Shopping cart sanitizing system by inventor Rhonda Holbrook published Aug. 21, 2007 the abstract discloses, "The present invention comprises a system and method for removing contaminates from the surface of a shopping cart such as a grocery cart. The system includes subjecting the cart to multiple stages of disinfection, including washing, sanitizing, and drying stages. A shopping cart is subjected to these stages by conveying the cart on a conveyor system past a plurality of nozzles, which are configured to provide a disinfecting fluid such as water, sanitizer or air. The invention uses sensors to detect the location of a shopping cart during the sanitizing process. The sensors provide indications of the cart's location which may be used to control the operation of the disinfecting stages on the conveyor belt."

For example, in United States publication number US20060011220A1 Shopping cart wash tunnel by inventor Rhonda Holbrook published Jan. 19, 2006 the abstract discloses, "A shopping cart sanitizing apparatus and method is provided that uses a wash tunnel to automatically dispense sanitizing agents onto shopping carts. The wash tunnel uses a conveyor or other means for moving shopping carts into the apparatus, where sanitizing agents are automatically dispensed onto the shopping carts. Suitable sanitizing agents include soap and water, chemical agents, or a combination of disinfecting fluids."

For example, in U.S. Pat. No. 7,516,967B2 Cart sanitizing system by inventor Mark C. Schwei published Apr. 14, 2009 the abstract discloses, "A cart sanitizing system is disclosed for applying a sanitizing fluid to sanitize a shopping cart. A pressurized supply of sanitizing fluid is applied to the cart contained within a cart enclosure through a series of spray nozzles mounted along a spray arch. The pressurized sanitizing fluid is supplied to the spray arch from a pressure tank, which is fed with the supply of sanitizing fluid from a chemical make-down system. The chemical make-down system creates the sanitizing fluid, which preferably includes a sanitizing agent and a surfactant mixed within fresh water. The sanitizing fluid is created by a mixing device by flowing the fresh water over inlet tubes for both the sanitizing agent and the surfactant. The mixture of the surfactant and sanitizing agent allows the sanitizing fluid to be applied to the shopping carts and eliminates the requirement for drying."

For example, in United States publication number US20080210268A1 Shopping Cart Washer and Sanitizer by inventor James R. Metheny published Sep. 4, 2008 the abstract discloses, "A shopping cart washer and sanitizer includes an enclosure fitted with components that facilitate the entry and exit of rolling shopping carts. Within the apparatus, the carts are washed, rinsed, disinfected and dried. The apparatus is primarily for use inside retail establishments and is intended to provide each shopper a clean and sanitary shopping cart. A shopping basket washer is also disclosed." The prior art references are incorporated herein by reference.

SUMMARY OF THE INVENTION

The present invention is a sanitizer for improving COVID 19 response. Coronaviruses can spread through contact on publicly used objects such as shopping carts and chairs. The present invention is designed to sanitize shopping carts and chairs which can be sanitized using soap, hydrogen peroxide, alcohol or other antibacterial liquid formulas in conjunction with ultraviolet light.

A moving tunnel sanitizer includes a frame forming a tunnel with a tunnel opening through the frame. A right wall supports a right side of the frame. A left wall supports a left side of the frame. A right front wheel and a right rear wheel support the right wall. A left front wheel and a left rear wheel supports the left wall. A top member makes a rigid connection between the right wall to the left wall. Nozzles are mounted on the tunnel on the right wall and on the left wall. A fluid tank stores a sanitizing fluid. The fluid tank is connected to the pump via fluid tubing, which is then connected to a valve for controlling flow, which is then connected to the nozzles.

A left motor and a right motor are drive motors. The left motor drives either the front left wheel or the rear left wheel. The right motor drives the front left wheel or the front right wheel.

A battery provides electrical power to the main control panel which then provides electrical power to the left motor and the right motor. The frame further includes a left front frame rib formed on the left wall at a left front edge and a right front frame rib formed on the right wall at a right front edge, wherein a front sensor mounted to a front portion of the frame provides a front collision avoidance function and wherein a rear sensor mounted to a rear portion of the frame provides a rear collision avoidance function.

The right wall also has a right tunnel panel, and the left wall has a left tunnel panel. The right tunnel panel has a right tunnel panel overlap connecting to the right front frame rib on the right wall, and the left tunnel panel has a left tunnel panel overlap connecting to the left front frame rib on the left wall. The right wall further includes a right side outer panel, and the left wall further includes a left side outer panel. The right side outer panel has a right side outer panel overlap connecting to the right front frame rib on the right wall, and the left side outer panel has a left side outer panel overlap connecting to the left front frame rib on the left wall.

The top member is formed of a top member frame sandwiched between a top panel frame cover below the top panel frame, and a top panel above the top panel frame. The top panel frame is connected to the right wall and the left wall. The nozzles are mounted on the top member facing downward, namely a top right nozzle and a top left nozzle. The nozzles are mounted on the right wall which include an upper right nozzle and a lower right nozzle. The nozzles are mounted on the left wall which include an upper left nozzle and a lower left nozzle.

A swivel platform is formed on a side of the right wall or the left wall. The swivel platform is hinged to rotate between a swivel platform stowed position and a swivel platform deployed position. A swivel manual control includes a CPU and data storage. The swivel manual control swivels from a swivel manual control stowed position within the frame to a swivel manual control deployed position. A front camera and a rear camera are connected to a client. The client is wirelessly connected through a mobile wireless transceiver to a base station wireless transceiver. The base station wireless transceiver is connected to a router. The router is connected to a wide area network. The wide area network makes a connection to a server.

A sprayer gun also fluidly connected to the fluid tank can spray sanitizing fluid and may have a UV light for local sterilization. The sprayer gun is connected to the moving tunnel sanitizer. The sprayer gun is configured to spray the sanitizing fluid.

The invention can also be stated as a method of sanitizing articles using a moving tunnel sanitizer which includes a series of steps of forming a frame with a tunnel and a tunnel opening through the frame; forming a right wall supporting a right side of the frame; forming a left wall supporting a left side of the frame; configuring a right front wheel and a right rear wheel supporting the right wall; configuring a left front wheel and a left rear wheel supporting the left wall; configuring a top member to make a rigid connection between the right wall to the left wall; mounting nozzles on the tunnel on the right wall and on the left wall; installing a fluid tank storing a sanitizing fluid; connecting the fluid tank to the nozzles; installing a left motor and a right motor so that the left motor drives either the front left wheel or the rear left wheel, and so that the right motor drives the front left wheel or the front right wheel; and installing a battery for providing electrical power to the left motor and the right motor.

The method of sanitizing articles can also be accomplished by forming a left front frame rib formed on the left wall of the frame at a left front edge and a right front frame rib formed on the right wall of the frame at a right front edge; mounting a right tunnel panel on the right wall, and mounting a left tunnel panel on the left wall; securing the right tunnel panel with a right tunnel panel overlap connecting to the right front frame rib on the right wall; and securing the left tunnel panel with a left tunnel panel overlap connecting to the left front frame rib on the left wall.

The method of sanitizing articles optionally includes the step of forming the top member with a top member frame sandwiched between a top panel frame cover below the top panel frame, and a top panel above the top panel frame; and the step of connecting the top panel frame to the right wall and the left wall. The method of sanitizing articles using a moving tunnel sanitizer may also include the step of mounting nozzles on the top member facing downward, namely a top right nozzle and a top left nozzle; mounting the nozzles on the right wall which include an upper right nozzle and a lower right nozzle; and mounting the nozzles mounted on the left wall which include an upper left nozzle and a lower left nozzle. The method of sanitizing articles using a moving tunnel sanitizer may also include the step of installing a swivel platform formed on a side of the right wall or the left wall; and configuring the swivel platform to rotate between a swivel platform stowed position and a swivel platform deployed position; and further configuring a swivel manual control to include a CPU and data storage and a joystick. The method of sanitizing articles using a moving tunnel sanitizer may also include the step of installing a front camera and a rear camera in connection with a client; the step of connecting a client to the front camera and the rear camera, the step of wirelessly connecting the client through a mobile wireless transceiver to a base station wireless transceiver; the step of configuring the base station wireless transceiver to connect to a router; and the step of further configuring the router to connect to a wide area network to connect to a server. The rear view camera can be a backup camera that automatically activates when moving and shows a backup view output on the user's screen.

The following call out list can be a useful guide for referencing the call out numbers of the drawings.

15 Top Member
16 Left Wall
17 Right Wall
18 Frame Front
19 Line Of Shopping Carts
20 Moving Tunnel Sanitizer
21 Frame
22 Right Rear Wheel
23 Right Front Wheel
24 Right Side
25 Warning Light
26 Receiving Port
27 Right Side Door Set
28 Direction Of Movement
29 Tunnel Opening
32 Left Rear Wheel
33 Left Front Wheel
34 Left Front Frame Rib
35 Right Front Frame Rib
36 Left Tunnel Panel
37 Right Tunnel Panel
38 Top Panel
39 Left Outer Panel
41 Upper Left Side Door Hinges
42 Lower Left Side Door Hinges
43 Right Side Panel Overlap
44 Right Side Outer Panel
45 Left Side Panel Overlap
46 Right Tunnel Panel Overlap
47 Left Tunnel Panel Overlap
50 Intake Roller Assembly
51 Left Roller Assembly
52 Right Roller Assembly
55 Left Roller Array
56 Right Roller Array
57 Left Roller Frame
58 Right Roller Frame
59 Roller Axle
60 Spray Nozzle Set
61 Top Left Nozzle
62 Top Right Nozzle
63 Upper Left Nozzle
64 Lower Left Nozzle
65 Upper Right Nozzle
66 Lower Right Nozzle
67 First Fluid Tank
68 Second Fluid Tank
69 Spray Line
70 First Battery Stack
71 First Battery
72 Second Battery
73 Third Battery
74 Fourth Battery
75 Swivel Manual Control
76 Swivel Platform
77 Swivel Back Rest
79 Telescopic Snap Connection
81 Joystick Control
82 Display Screen
83 Control Buttons
84 Swivel Mounted Control Panel
85 Backrest First Swivel
86 Back Rest Second Swivel
87 Platform Swivel
88 Sprayer Gun
89 Sprayer Gun Support
90 Top Panel Frame
91 Top Panel Frame Cover
92 Left Rear Door
93 Left Middle Door
94 Left Door Strut
95 Left Front Door
96 Left Front Edge
97 Right Front Edge
100 Fluid Flow
101 Fluid Stream
102 Fluid Nozzle
103 Electrostatic Charge Wire
104 Hose Connection
105 Fluid Sensor
106 Gun Sensor
107 Gun Grip Handle
108 Nozzle Opening
109 Inside Wheel
110 Outside Wheel
111 Motor Shaft
112 Gear Box
113 Speed Control
114 Left Upper Roller Frame
115 Left Lower Roller Frame
116 Second Battery Stack
117 Roller Direction
118 Top Roller Roll
119 Middle Roller Row
120 Bottom Roller Row
121 Roller Stack Unit
122 Hose
123 Ultraviolet LED (light-emitting diode)
124 Tow Connector
125 Front Sensor
126 Rear Sensor
127 Front Camera
128 Rear Camera
129 Bumper Sensor
140 Motors
141 Right Rear Motor
142 Left Rear Motor
143 Right Front Motor 144 Left Front Motor
145 Right Underbody LED Light
146 Left Underbody LED Light
147 Tunnel Lamp
148 Right Front LED Light
149 Left Front LED Light
150 Client
151 Mobile Wireless Transceiver
152 CPU (Central Processing Unit)
153 Data Storage
154 Base Station Wireless Transceiver
155 Router Or Modem
156 Wide Area Network
157 Server
158 Second Base Station
159 Battery Level Sensor
160 Sanitizing Fluid

DETAILED DESCRIPTION OF THE PREFERRED EMBODIMENT

Figure 1:
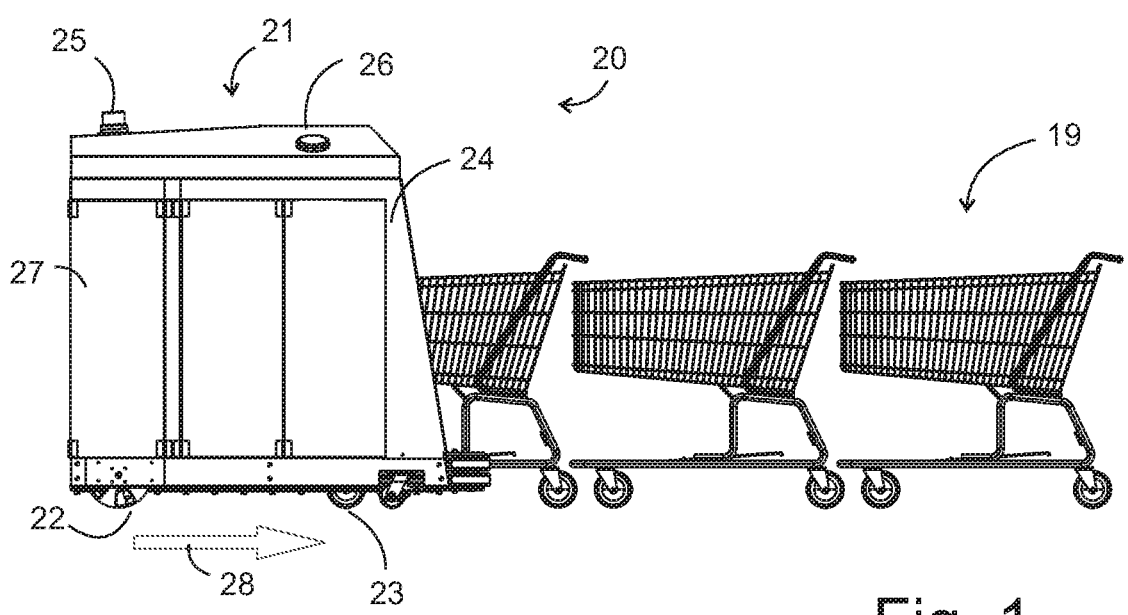
FIG. 1 is a side view diagram showing the moving tunnel sanitizer processing a stacked line of shopping carts.

As seen in FIG. 1, a moving tunnel sanitizer 20 is passing over a line of shopping carts 19. The moving tunnel sanitizer 20 has a frame 21 driven by a right rear wheel 22, a right front wheel 23, a left rear wheel 32, and a left front wheel 33. The moving tunnel sanitizer 20 is a vehicle that can be four-wheel-drive. The rear wheels and/or the rear wheels of the moving tunnel sanitizer 20 can be formed as split wheels having a right wheel section and a left wheel section with a motor between them.

The frame 21 has a right side 24 upon which is mounted the right side door set 27. Similarly, the left side has a left side door 31. On the top portion of the frame 21, a warning light 25 is preferably made as a strobe light which activates during movement and has a beeping sound. The strobe bright and beeping apparatus provided a safety mechanism when backing up. A receiving port 26 allows users to introduce cleaning or sanitizing fluid 160 into the moving tunnel sanitizer 20. Cleaning fluid can be hydrogen peroxide, bleach or the like such as soap, alcohol or other antibacterial liquid formulas. The frame 21 is configured to move forward in the direction of movement 28, but the direction of movement 28 can also be backwards. The tunnel opening 29 is preferably sized for being able to receive shopping carts.

Figure 2:
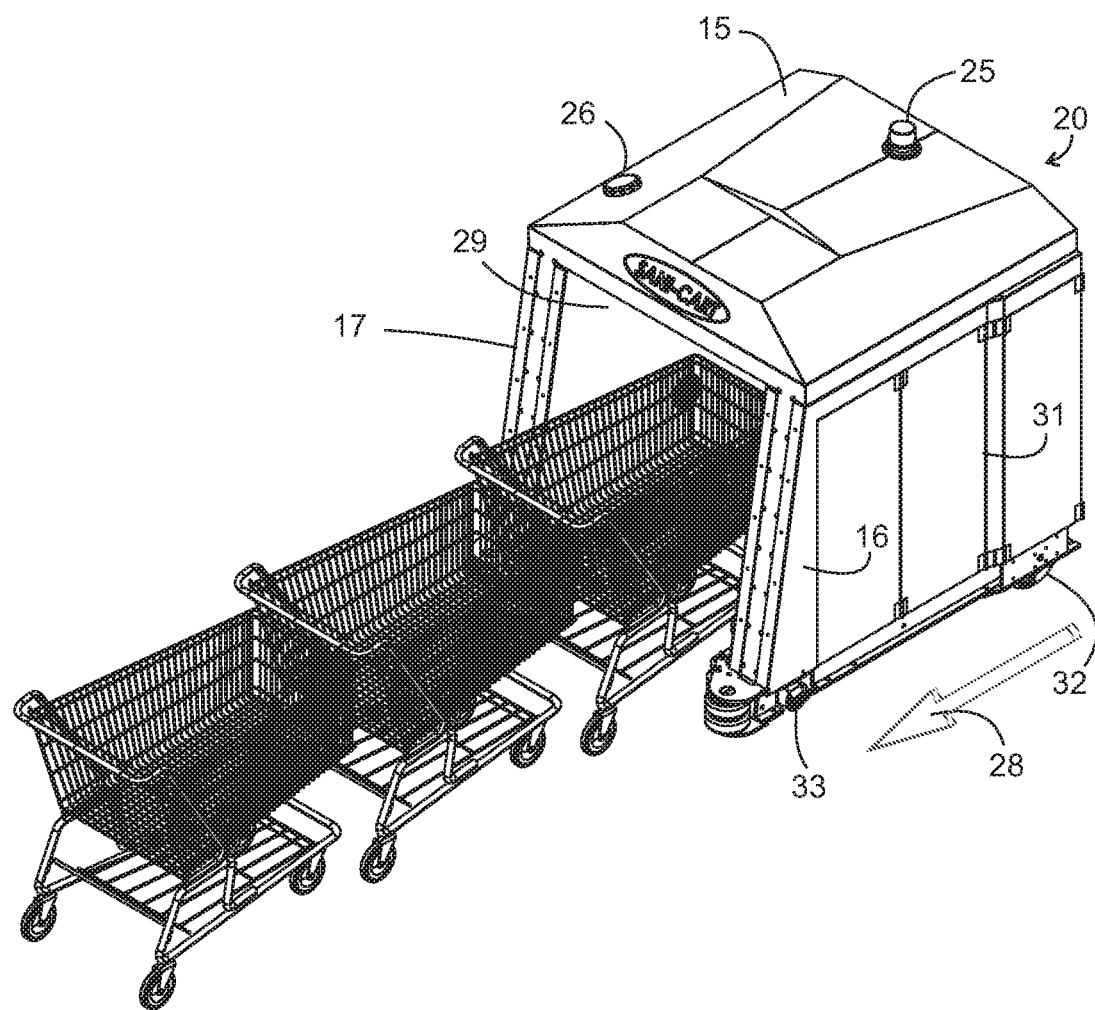
FIG. 2 is an isometric diagram showing the moving tunnel sanitizer processing a line of shopping carts.

As seen in FIG. 2, the moving tunnel sanitizer 20 has a warning light 25 and a receiving port 26 are mounted on a top portion. The moving tunnel sanitizer 20 generally has a left wall 16 and a right wall 17 with a top member 15 connecting the left wall to the right wall. The top member 15 is formed as a roof and flat ceiling providing rigid structure between the left wall and the right wall. The left wall 16 and the right wall 17 form a pair of pier supports upon which the top portion is mounted. The moving tunnel therefore covers the top, left and right sides of the articles being sanitized.

The left side of the left wall has a left side door 31. The left side door 31 is formed on the left outer panel 39. The moving tunnel sanitizer 20 can be driven by the left rear wheel 32 and the left front wheel 33. The doors are mounted on hinges. The upper left side door hinges 41 and the lower left side door hinges 42 control movement of the left side doors.

Figure 3:
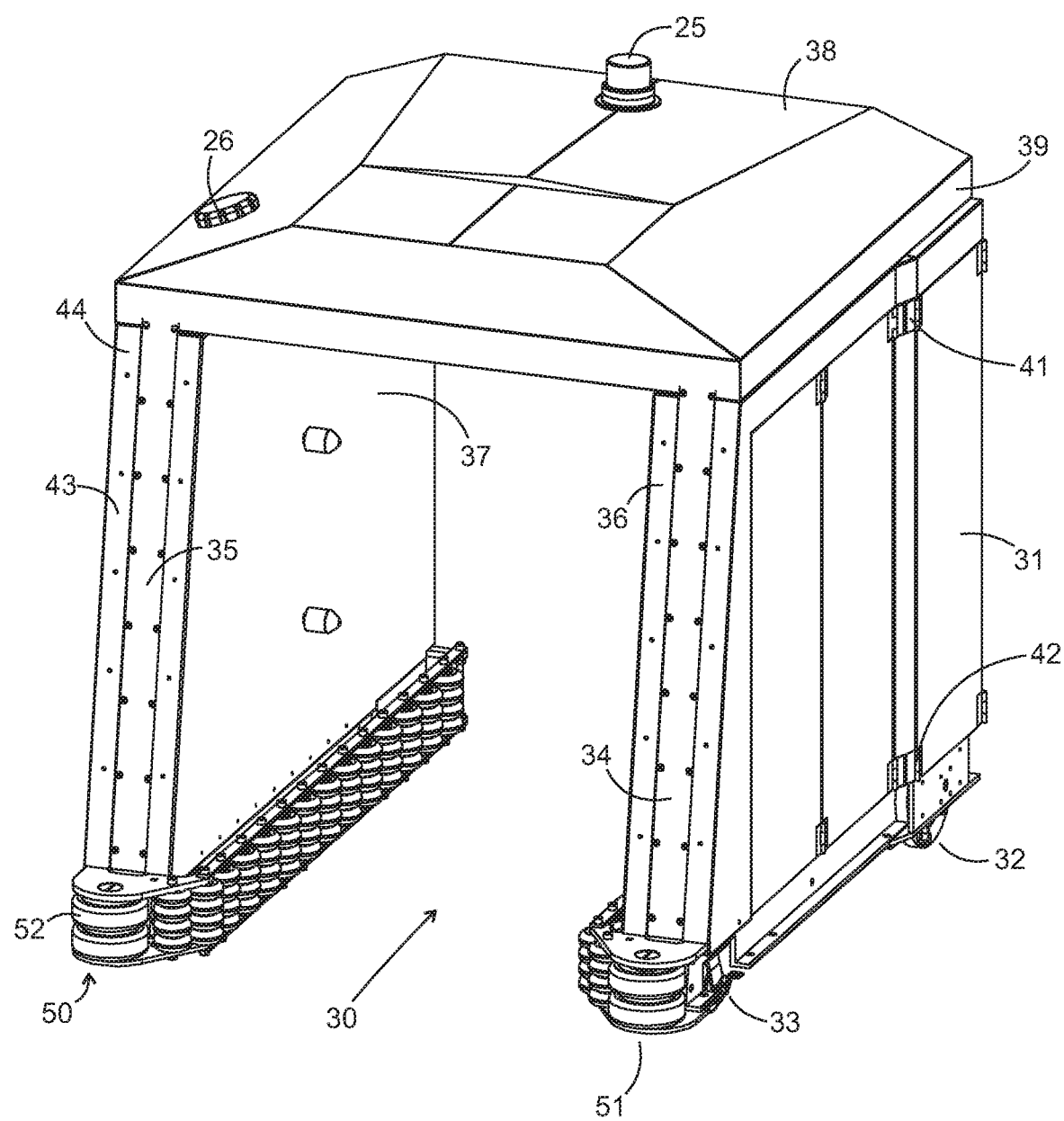
FIG. 3 is an isometric diagram showing the tunnel of the moving tunnel sanitizer.

As seen in FIG. 3, the tunnel 30 is large enough for shopping carts, so could also sanitize chairs, benches and the like even when stacked. The left rear wheel 32 can cooperate with the left front wheel 33 being microprocessor controlled to allow tight turning. The left front frame rib 34 and the right front frame rib 35 are angled to provide rigidity to a left tunnel panel 36 secured to the left side of the tunnel 30, and a right tunnel panel 37 secured to the right side of the tunnel 30. A top panel 38 is preferably made of stamped or bent stainless steel sheeting or paneling. The front frame ribs receive the side panels. A right side panel overlap 43 formed on the right side outer panel 44 secures to the right front frame rib 35. A left side panel overlap 45 formed on the left outer panel 39 secures to the left front frame rib 34.

An intake roller assembly 50 includes a left roller assembly 51 and a right roller assembly 52. The intake roller assembly 50 is mounted near the ground to align articles to be sanitized. When configured for shopping carts, the intake roller assembly 50 is mounted at a lower portion of the moving tunnel sanitizer 20 to align the line of shopping carts along the shopping cart wheels.

Figure 4:
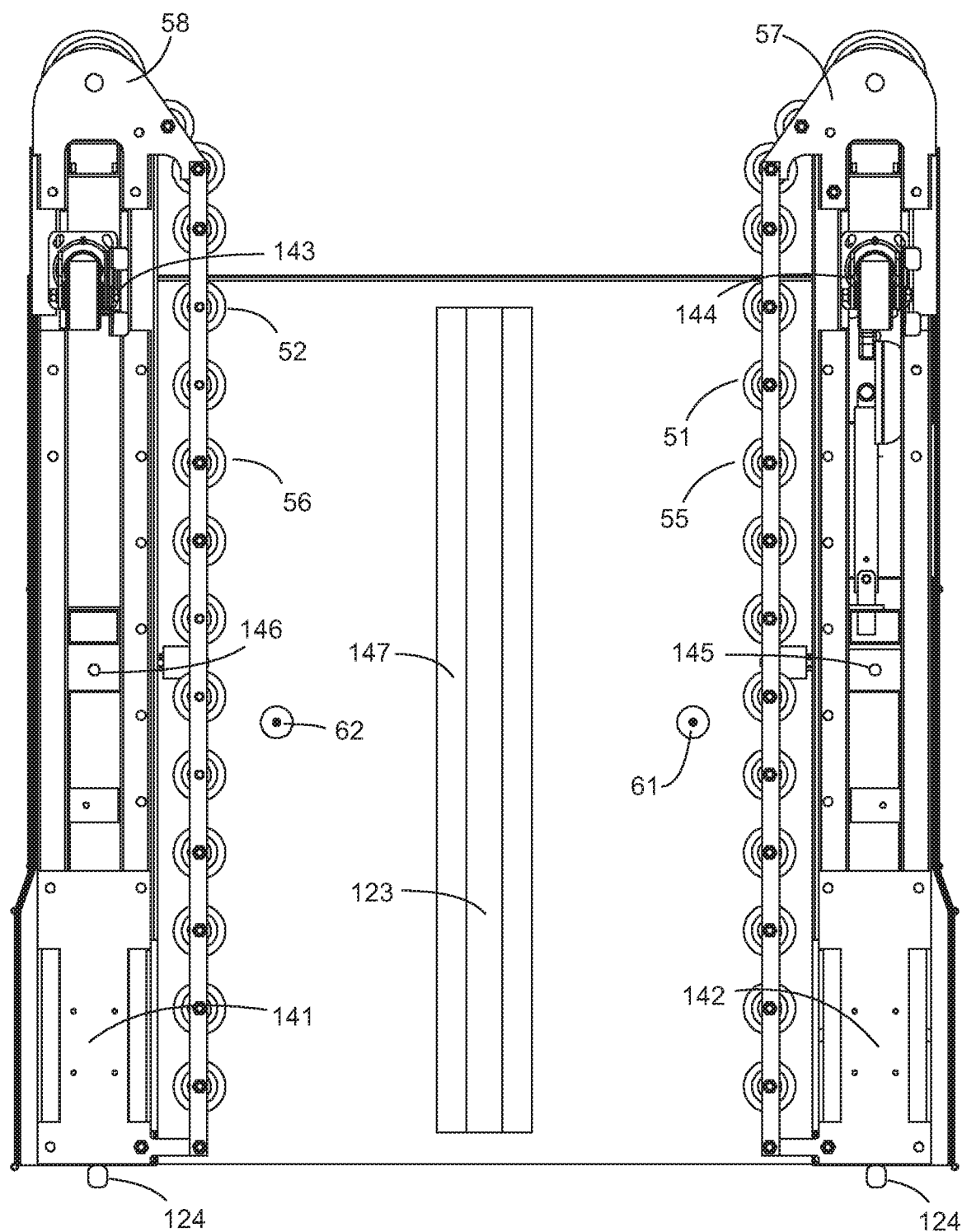
FIG. 4 is a bottom view of the present invention.

As seen in FIG. 4, a bottom view shows the left roller assembly 51 has a left roller array 55, and the right roller assembly 52 has a right roller array 56. The left roller assembly 51 is mounted on the left roller frame 57, and the right roller assembly 52 is mounted on the right roller frame 58. During movement of the moving tunnel sanitizer, the right underbody LED light 145 and the left underbody LED light 146 are lighted to indicate that the moving tunnel sanitizer Drive motors are active. The underbody LED lights can be formed as twelve volt light-emitting diode strips and could either be wired in parallel with the drive motors for the wheels, or could be controlled by the central processing unit in the control panel. A tunnel lamp 147 faces downwardly and illuminates the articles being sprayed so that the spray mist that exits from the front and rear openings of the tunnel becomes visible. A tow connector 124 can provide a latching area for towing the carts. Preferably, tow connectors 124 can be mounted to the rear part of the left and right walls.

The wheels are driven by motors. A left motor and a right motor are respectively mounted on the left and right walls. The left motor drives either the left front wheel or the left rear wheel, and the right motor drives the right front wheel or the right rear wheel. A set of motors 140 may include a right rear motor 141, a left rear motor 142, a right front motor 143 and a left front motor 144. If the front wheels are caster wheels, two motors can drive the rear wheels and the front motors can be omitted.

Figure 5:
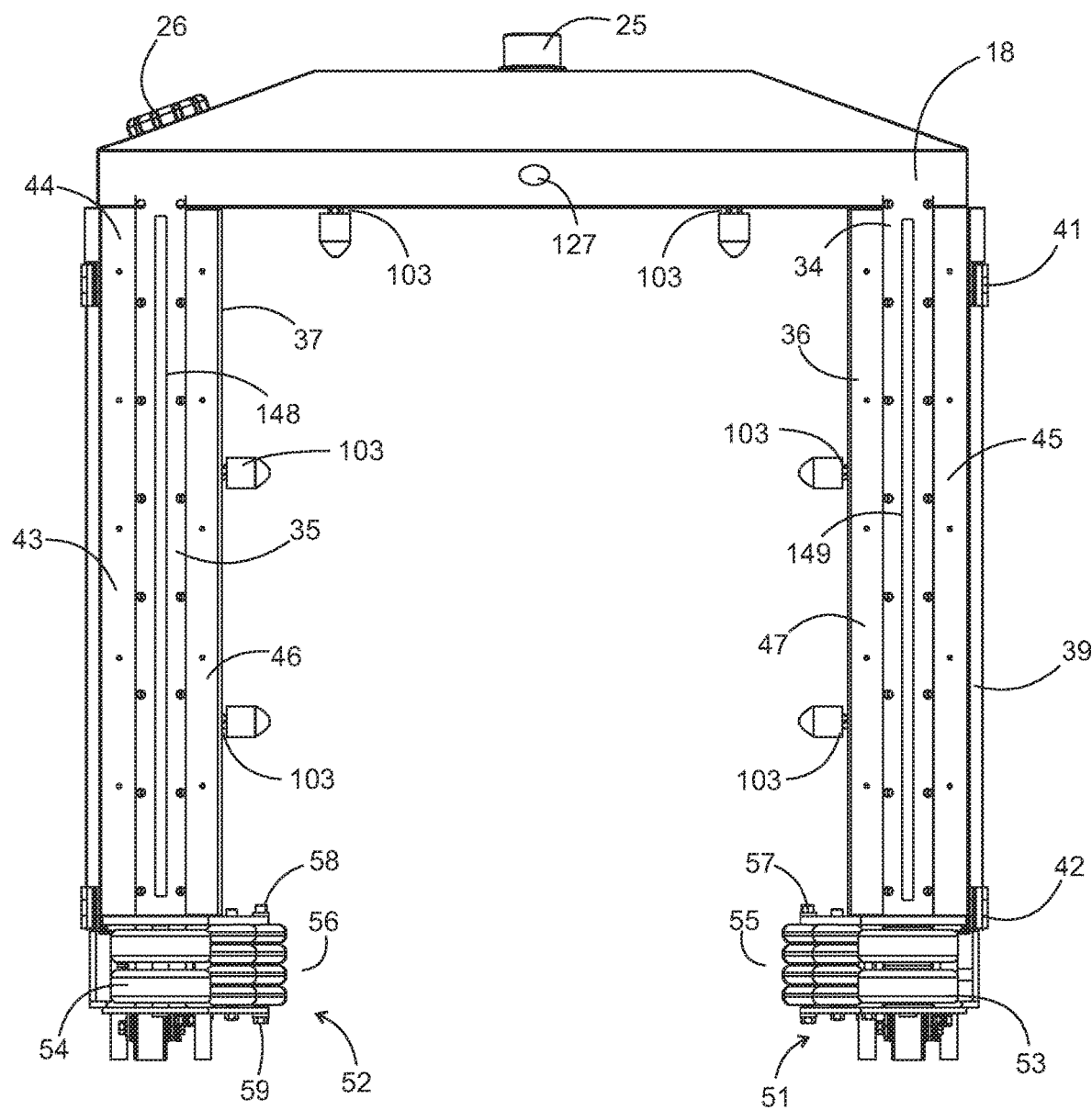
FIG. 5 is a front view of the present invention.

As seen in FIG. 5, the frame front 18 provides structure for the frame 21. The left front frame rib 34 is secured to the left tunnel panel overlap 47 of the left tunnel panel 36, and also secured to the left side panel overlap 45 of the left outer panel 39. The right front frame rib 35 is secured to the right tunnel panel overlap 46 of the right tunnel panel 37, and also secured to the right side panel overlap 43 of the right side outer panel 44. The frame front 18 thus stabilizes the pair of roller assemblies, namely the left roller assembly 51 and the right roller assembly 52.

The left front roller 53 of the left roller assembly and the right front roller 54 of the right roller assembly are larger than the rollers on the left roller array 55 and the right roller array 56. The relative diameter ratio can be 2:1 between the front rollers and the rollers on the roller array. The front rollers and the rollers on the roller array are formed in stacks secured on roller axles 59 that are preferably bolted to the left roller frame 57, and the right roller frame 58.

The rigidity provided by the frame front 18 also is important for maintaining alignment of the doors to the door hinges such as the upper left side door hinges 41 and the lower left side door hinges 42. The frame front 18 also has a pair of front LED lights which provide illumination during driving, and also activate such as by intermittent flashing during sanitation spraying. The pair of front LED lights include a right front LED light 148 and a left front LED light 149.

Each of the nozzles preferably have an electrostatic charge wire 103 mounted to them for electrostatically charging the spray mist sprayed from the nozzles. During spray, the pair of front LED lights is preferably activated and can be flashing to indicate that the nozzle pump is active. The pair of front LED lights can be controlled through the central processing unit or controlled by being wired in parallel to the fluid pumps.

Figure 6:
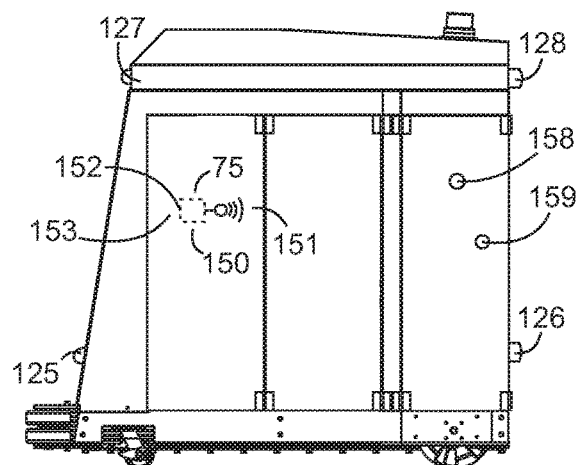
FIG. 6 is a left side view.
Figure 7:
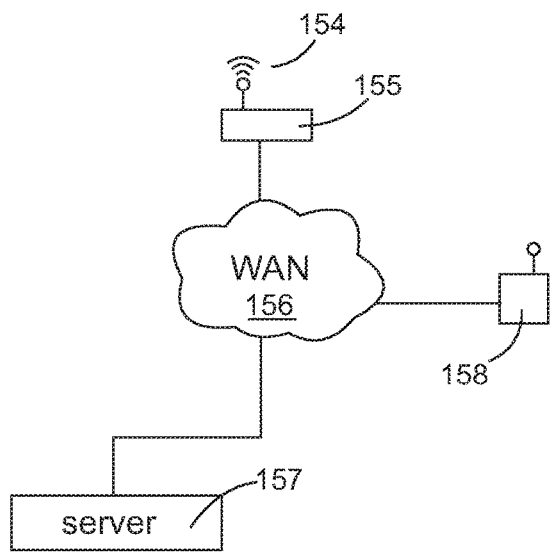
FIG. 7 is a right side view.
Figure 7:
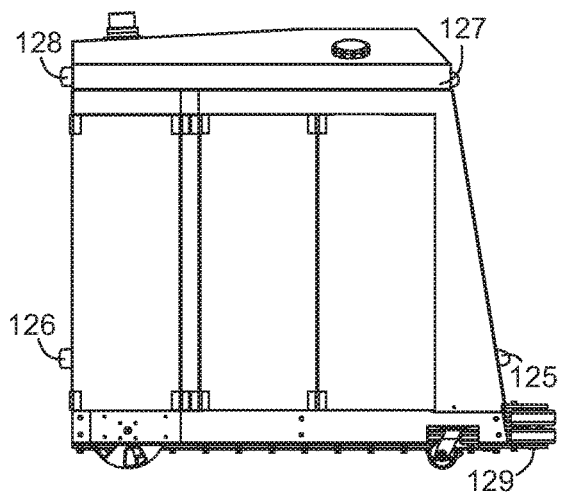

Maintaining a dimensional stability provides the moving tunnel sanitizer 20 with a rigid structure so that the left side as seen in FIG. 6 is generally symmetrical to the right side as seen in FIG. 7. As seen in FIGS. 6, 7, during normal use of the moving tunnel sanitizer, the user can control the moving tunnel sanitizer with a mobile device such as a smart phone. The moving tunnel sanitizer 20 can have a towing connector such as a tow connector 124 mounted on a rear face of the frame of the moving tunnel sanitizer 20 to allow towing of shopping carts during sanitation. During remote control with a mobile device, the user can use the front camera 127 and the rear camera 128 to navigate. A rear sensor 126 and a front sensor 125 can provide collision avoidance. The rear sensor 126 and the front sensor 125 can be ultrasonic proximity sensors. One or more bumper sensors 129 can be a strain sensor mounted on the front wheels at a flat portion of the left roller frame 57 or the right roller frame 58.

As seen in FIGS. 6, 7, each of the swivel mounted manual controls 75 can have a client 150 having an enabled CPU 152 enabled with a data storage 153. The mobile wireless transceiver 151 of the client 150 can communicate with a base station wireless transceiver 154. The base station wireless transceiver 154 is connected to a router or modem 155. The router or modem is connected to the wide area network 156 which can be the Internet. The wide area network allows connection to a second base station 158 and a server 157. The server 157 provides a centralized management of all of the clients 150 and each client 150 receives data input from the front sensor 125, the rear sensor 126, though front camera 127, and the rear camera 128. The server 157 can also receive the data input from the client 150 regarding the bumper sensor 129, battery level sensor 159 and fluid level sensor 158 and the gun sensor 106. Thus, because each moving tunnel sanitizer 20 vehicle has a client 150, an administrator user at the server can control an entire fleet of moving tunnel sanitizers at different remote locations such as at different locations of food shopping areas for food handling areas. The router or modem can connect wirelessly such as through 3G wireless protocol using a cellular module. A gateway can be a modem or router. The gateway connects to the Internet.

Figure 8:
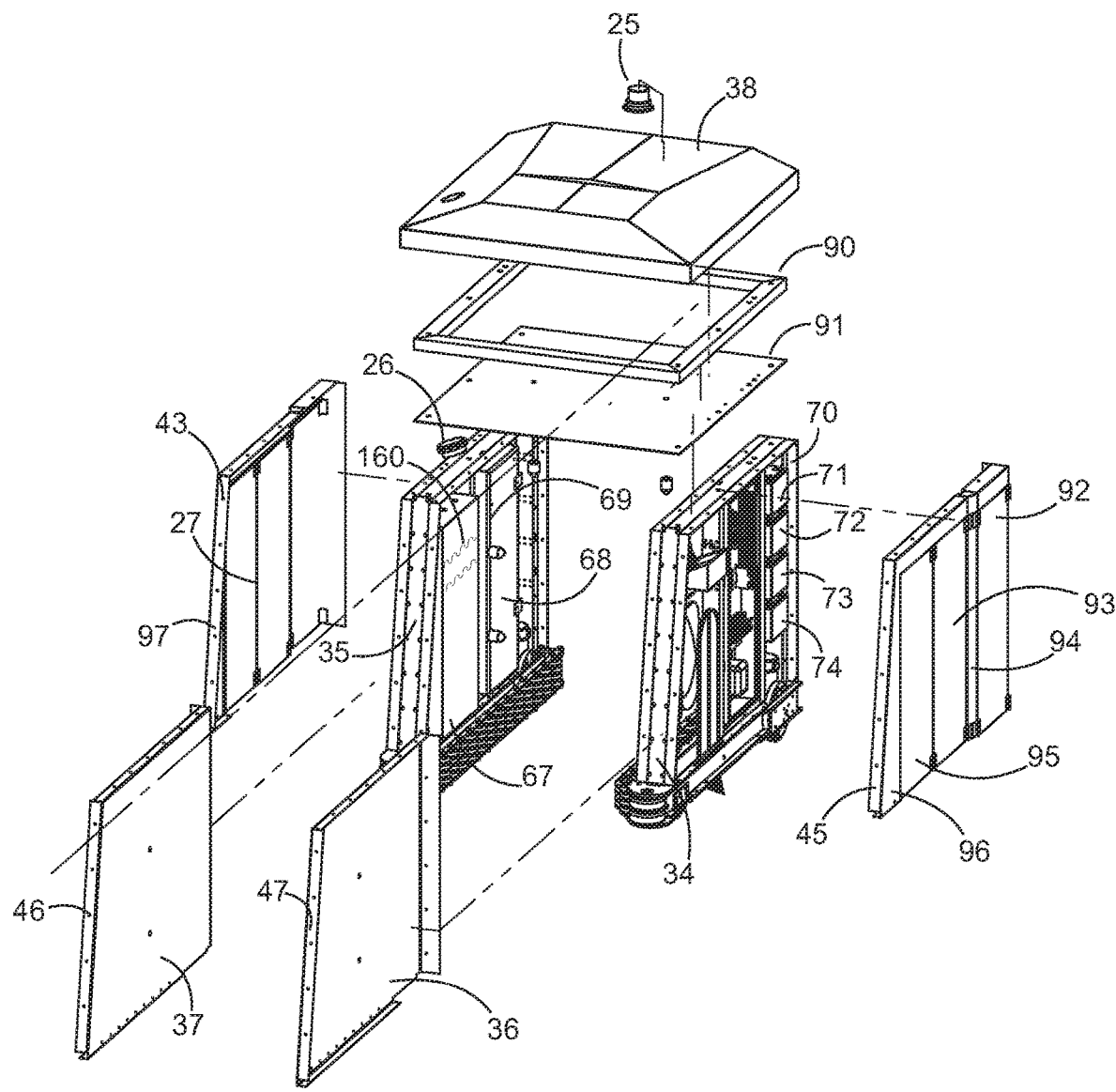
FIG. 8 is an exploded isometric view of the person invention showing construction of the moving tunnel sanitizer.

As seen in FIG. 8, an exploded view of the present invention shows the frame rigidity structure. The top panel frame 90 is a steel rectangular frame sandwiched between the top panel 38 and the top panel frame cover 91. The laminate reinforcement of an upper and lower side of the top panel frame 90 provides additional rigidity when connecting to the rest of the frame. The top panel frame cover 91 is formed as a sheet or plate of steel, and the top panel 38 has a concave cover that provides bending stability.

Besides the left front frame rib 34 and the right front frame rib 35, the frame 21 also includes a left door strut 94 and a right door strut. The left door strut 94 is vertically oriented and supports the left rear door 92, the left middle door 93, and the left front door 95. The left front edge 96 is generally vertical, at an angle. The left door strut 94 also provides structure for the first battery stack 70 which includes a first battery 71, a second battery 72, a third battery 73, and a fourth battery 74. Preferably, the left door strut 94 is bolted to the top panel frame cover 91 and the top panel frame 90.

The right side has a similar construction to the left side. The right side door set 27 is similarly supported by the right door strut, which also doubles for stabilizing the first fluid tank 67, and optionally a second fluid tank 68. The fluid tanks can be filled to a level that counterbalances user weight on the other side of the vehicle. The spray line 69 can also be mounted on the right door strut so that the spray line 69 carries fluid from the tanks to the nozzles. Each of the nozzles may have its own fluid pump for pumping liquid. The fluid pumps can be controlled by the client 150 at the swivel manual control 75. The left front frame rib 34 and the right front frame rib 35, which stabilizes the left tunnel panel 36, and right tunnel panel 37 at the right tunnel panel overlap 46 and the left tunnel panel overlap 47, are therefore both rigidly connected to the left door strut 94 and the right door strut when the left tunnel panel 36, and right tunnel panel 37 are bolted to the left door strut 94 and the right door strut.

The right side panel overlap 43 and the left side panel overlap 45 can be made by a bending brake on thick gauge stainless steel sheeting. The first fluid tank 67, the second fluid tank 68, receiving port 26, and the spray line 69 can be made by high density polyethylene material. The right front edge 97 is parallel to the left front edge.

Figure 9:
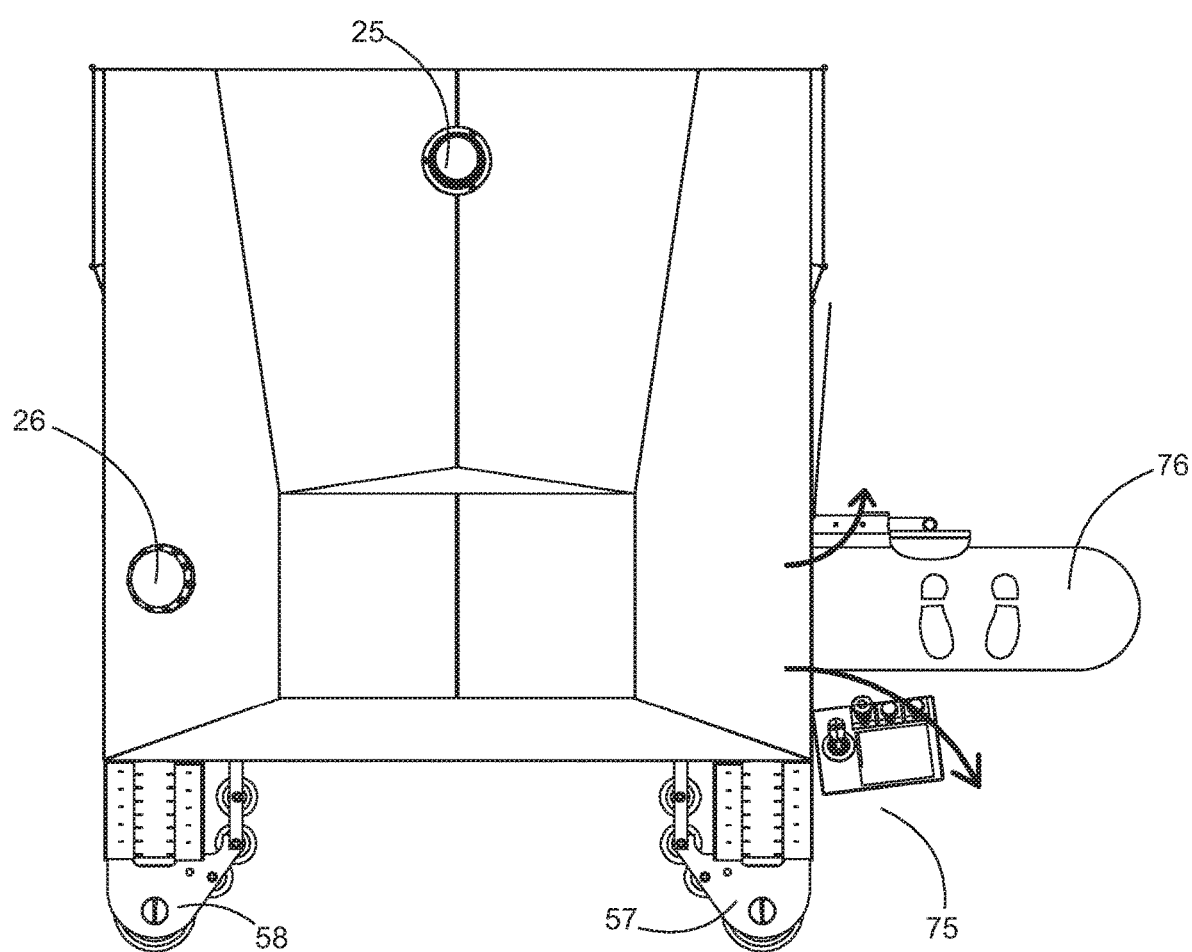
FIG. 9 is a top view of the deployed swivel platform.

Operation of the moving tunnel sanitizer is shown in FIG. 9. The first step in operating the tunnel sanitizer is to activate the control panel using a key. The key can be a mechanical key, a software key, or an RFID tag. Alternatively, the control panel can have a password access and a central processing unit of the control panel can facilitate the password access. The control panel has controls that allow different modes of operation. In a first mode, the vehicle is drive only without spray and has a faster driving speed, and in a second mode, the vehicle activates a spray and the vehicle has a slower preset speed in the second mode. In a third mode, the vehicle operates the spray gun. The regular driving speed is faster than the slower preset speed. The modes are mutually exclusive to each other and can be selected by turning a dial, or a key to a particular angle to select the mode.

In the second mode, the vehicle moves at the preset speed and after a preset time such as 3 seconds, the control panel will begin spraying by activating the fluid pumps, or will provide an indication of an error. The vehicle has a zero turn radius. The control panel provides control for wheel movement so that the vehicle has no turn radius.

When the swivel platform 76 unfolds from a vertical stowed position to a horizontal deployed position, the warning strobe light 25 activates to indicate user operation. The warning strobe light also activates when the fluid level is too high, or too low, when a door is open, or when other abnormal conditions exist for the moving tunnel sanitizer. The user also folds the swivel manual control 75 from a folded stowed position to an unfolded deployed position. The user stands on the swivel platform 76 and drives the moving tunnel sanitizer using the swivel manual control 75. The left roller frame 57 and the right roller frame 58 are formed as funnels with beveled angular faces to funnel shopping carts through the tunnel. The user drives the moving tunnel sanitizer over the carts, while the beveled angular faces ensure alignment of the line of carts.

Figure 10:
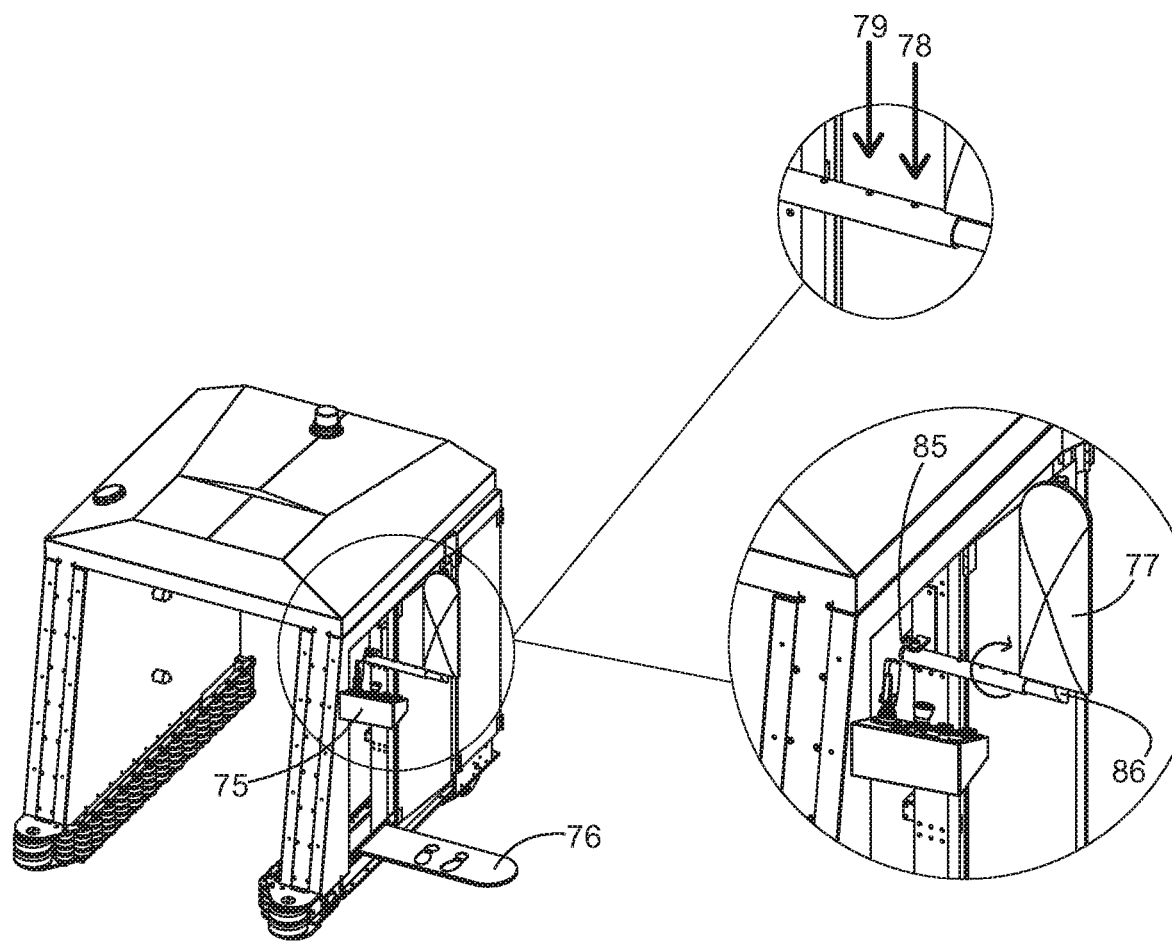
FIG. 10 is an isometric view with detailed views of the deployed lumbar backrest.

As seen in FIG. 10, the user also has a swivel back rest 77 to provide stability for the user while controlling the vehicle with the swivel manual control 75 and while standing on the swivel platform 76. The swivel back rest 77 also has a swivel backrest stowed position and a swivel backrest deployed position. The swivel backrest has a swivel backrest extension arm 78 preferably with a telescopic snap connection 79 to allow extension support and adjustment. The user can lean back on the swivel backrest 77 while standing. The swivel backrest 77 braces the user's torso, to allow the user to control using the swivel manual control 75. The swivel backrest 77 has a backrest first swivel 85 that swings outwardly, and also a back rest second swivel 86 that swings upwardly. The swivel backrest 77 thus has a pair of swivels that allow stowage of the swivel backrest in an upside down vertical position.

Figure 11:
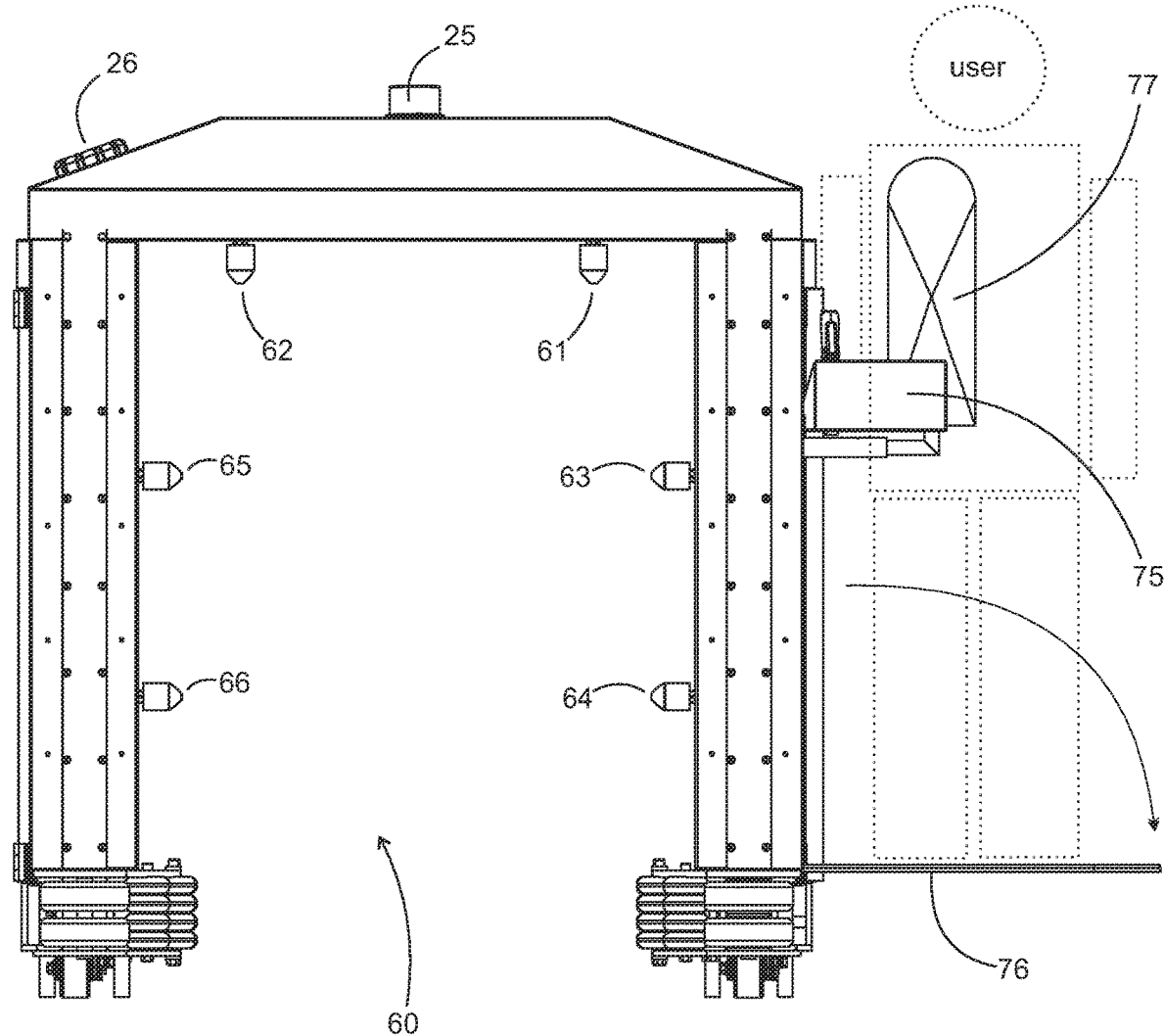
FIG. 11 is a front view of the invention with the deployed swivel platform.

As seen in FIG. 11, a spray nozzle set 60 sprays cleaning mist or liquid over the line of shopping carts. The spray nozzle set 60 has a top left nozzle 61, a top right nozzle 62, an upper left nozzle 63, a lower left nozzle 64, an upper right nozzle 65, and a lower right nozzle 66. The warning strobe light 25 could have a different flashing pattern when the spray nozzles are activated. A liquid pump pressurizes the spray nozzles for spraying the line of shopping carts. The warning strobe light 25 can also activate when the cover of the receiving port 26 is removed, or when liquid levels are low. The front view of the swivel platform 76 and the swivel manual control 75 shows that the swivel back rest 77 is aligned to a right shoulder of the user so that the user's right arm is stabilized in the forward and backward direction.

Figure 12:
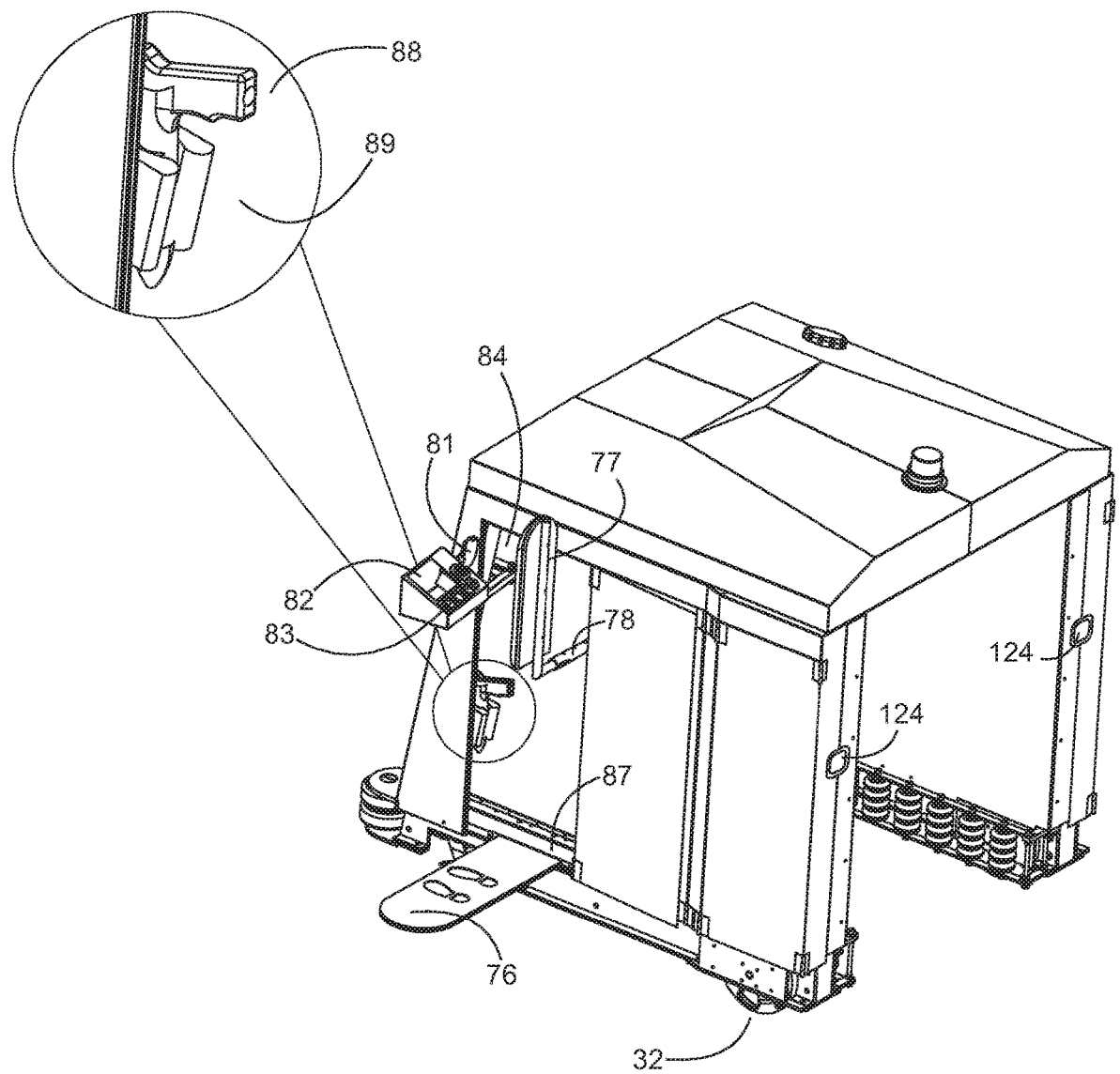
FIG. 12 is a rear side isometric view showing the storage of the sprayer gun and the holster.

As seen in FIG. 12, the swivel mounted control panel 84 has a joystick control 81, display screen 82, and control buttons 83. The control panel 84 controls the wheels, such as the left rear wheel 32. A hollow storage cabinet allows storage of the swivel platform 76, the swivel back rest 77, the swivel backrest extension arm 78. The swivel platform 76 swivels on the platform swivel 87, which can be formed as a hinge with a hinge stop. The hollow storage cabinet formed on the left side of the vehicle also has a sprayer gun 88 holstered in a sprayer gun support 89. The sprayer gun 88 allows the user to sanitize a wide variety of objects such as food, people and structures such as trash cans. The sprayer gun 88 may have a high intensity ultraviolet LED 123 for ultraviolet sanitation. The sprayer gun 88 could be used for sanitizing the user, and the vehicle before and after use.

Figure 13:
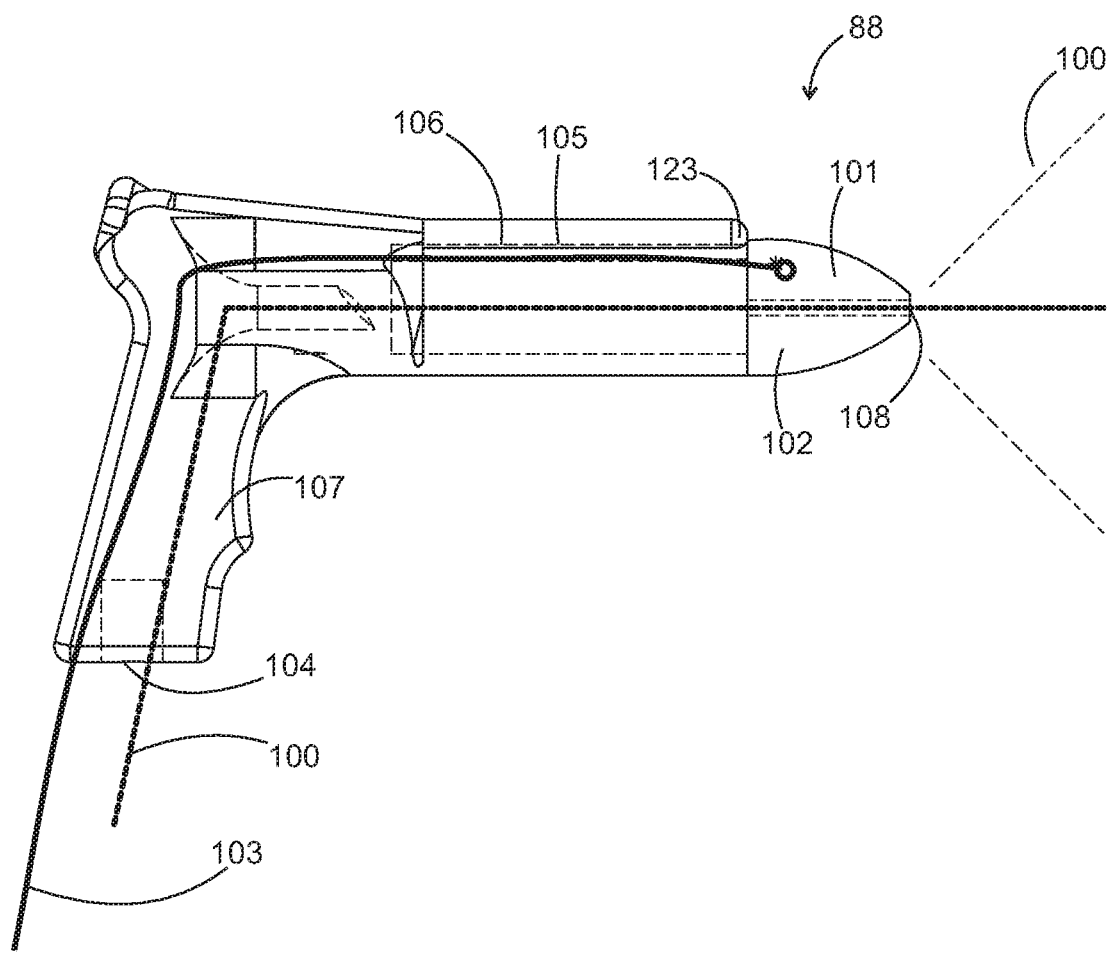
FIG. 13 is a cross section view of the sprayer gun.

As seen in FIG. 13, the sprayer gun 88 is configured to emit a fluid flow 100 in a fluid stream 101 from a fluid nozzle 102. The sprayer gun 88 preferably has an electrostatic charge wire 103 mounted to the fluid nozzle 102. The electrostatic charge wire 103 provides an electrostatic charge to the flow of fluid passing through the spray gun 88. The nozzles also have an electrostatic charge wire mounted to them. The electrostatic charge wire 103 provides a negative electrical charge to the fluid. The electrostatic charge wire 103 has a voltage of 10,000 V at low current with a current limiting circuit.

The hose connection 104 is preferably a threaded connection for carrying the fluid flow 100. A fluid sensor 105 can sense a pressure or fluid flow 100. The warning light can flush with a different pattern when the sprayer gun 88 is in use. The fluid sensor 105 and the gun sensor 106 can provide data to a central processing unit on the control panel. The control panel is preferably wirelessly connected such as by IEEE 802.11ac, Wi-Fi or the like to the wireless network of the building facility where the vehicle is being used. The central processing unit can be on a PC (personal computer) that is a client. The client can connect to the server over a wide area network such as the Internet. Thus, the server can monitor use of the sprayer gun 88 via sensors such as the fluid sensor 105 or the gun sensor 106. The sprayer gun 88 preferably also has an ergonomic gun grip handle 107 and adjustable nozzle opening 108 for different spray patterns. The different spray patterns can be coordinated with the high intensity ultraviolet LED 123 for ultraviolet sanitation. For example, the ultraviolet LED 123 can be automatically activated when the sprayer gun 88 is activated in a particular mode.

Figure 14:
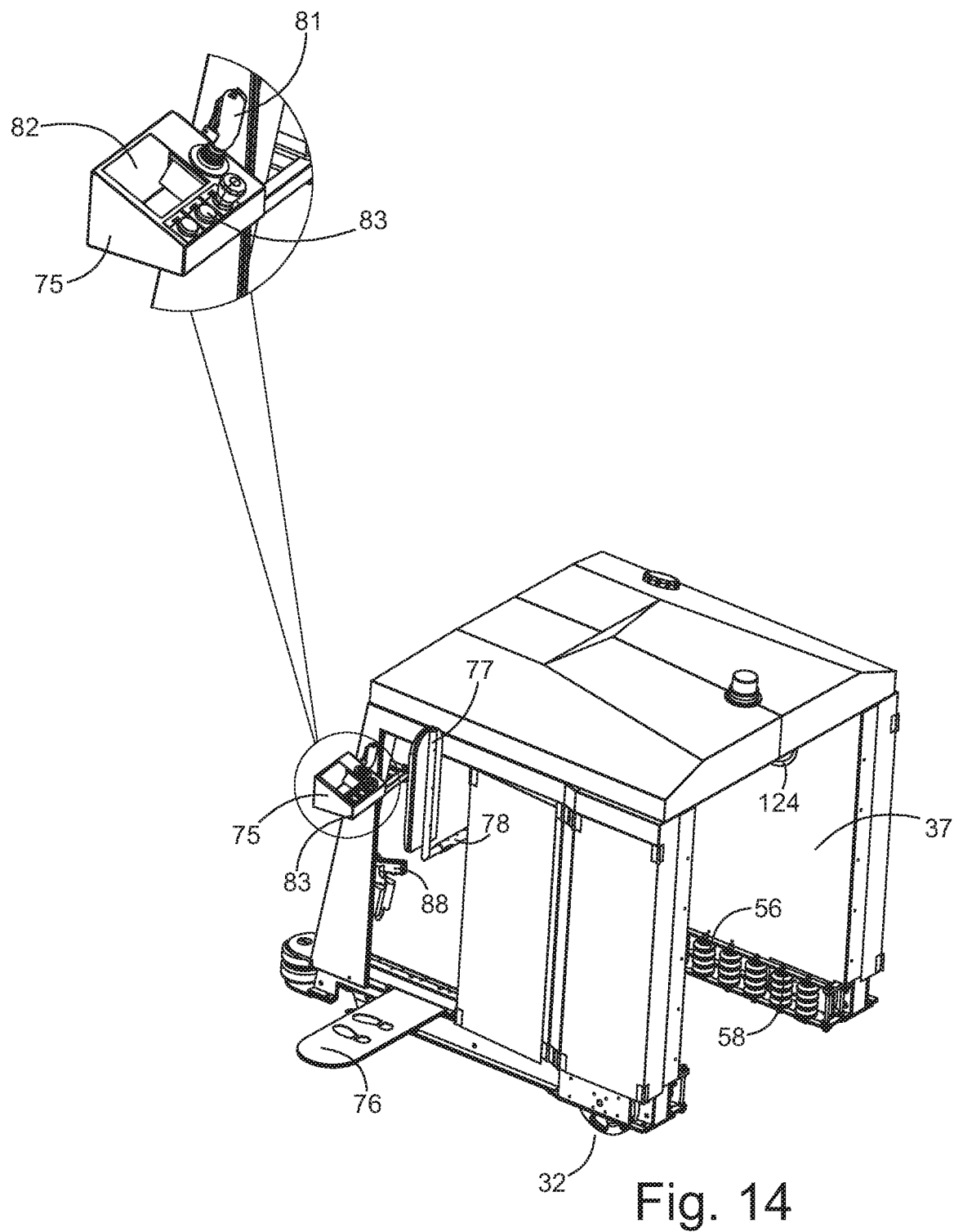
FIG. 14 is a isometric view showing detail for the joystick, control buttons, and a human machine interface touch panel with graphic user interface.

As seen in FIG. 14, the sprayer gun 88 is preferably controllable using the control panel. The control panel may have a touchscreen that allows selection of different modes of operation for the sprayer gun 88. The touchscreen can also provide diagnostic information on the spray gun 88 based upon logs of sensors. Therefore, the control panel preferably also includes a storage device with a database so as to store the data logs.

The control buttons 83 also allow operation of the control panel to access logs of the usage of the vehicle including vehicle runtime, fluid levels, usage logs, and the like. The data logs are stored locally and also can be provided to the server for central administration and management of a fleet of moving tunnel sanitizers 20. After use, the user folds up the deployed backrest, platform and control panel and can plug in the vehicle so that the battery stacks are recharged overnight. Depending upon frequency of use, deep cycle batteries such as lithium iron phosphate LiFePo batteries can be selected for the battery stacks.

The swivel manual control 75 has a joystick control 81, display screen 82, and control buttons 83 for receiving control inputs. The swivel platform 76 mounted on the platform swivel 87 is formed as a flat planar plank with a rounded end. The swivel back rest 77 with extended swivel backrest extension arm 78 can be padded for extra comfort. The sprayer gun 88 is typically stowed when not in use.

Figure 15:
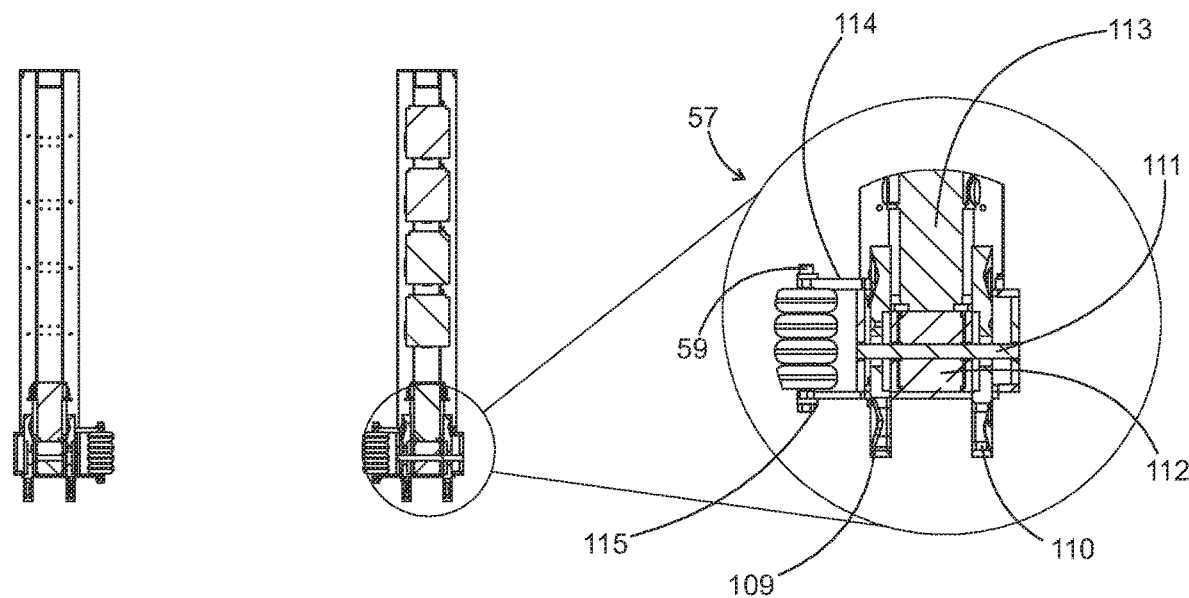
FIG. 15 is a cross section view of the wheel assembly.

As seen in FIG. 15, a left roller frame 57 retains a roller axle 59. The left rear wheel is split into an inside wheel 109, and an outside wheel 110. The roller axle 59 can be directly driven with a motor shaft 111, or can be driven indirectly through a gear box 112. In any case, an electronic speed control 113 such as a pulse width modulated speed control (PWM) could receive a control signal from the joystick and output to the motor shaft one 111. The motor is preferably mounted next to the roller stack. The roller stack is held between the left upper roller frame 114 and the left lower roller frame 115 of the roller left frame.

Figure 16:
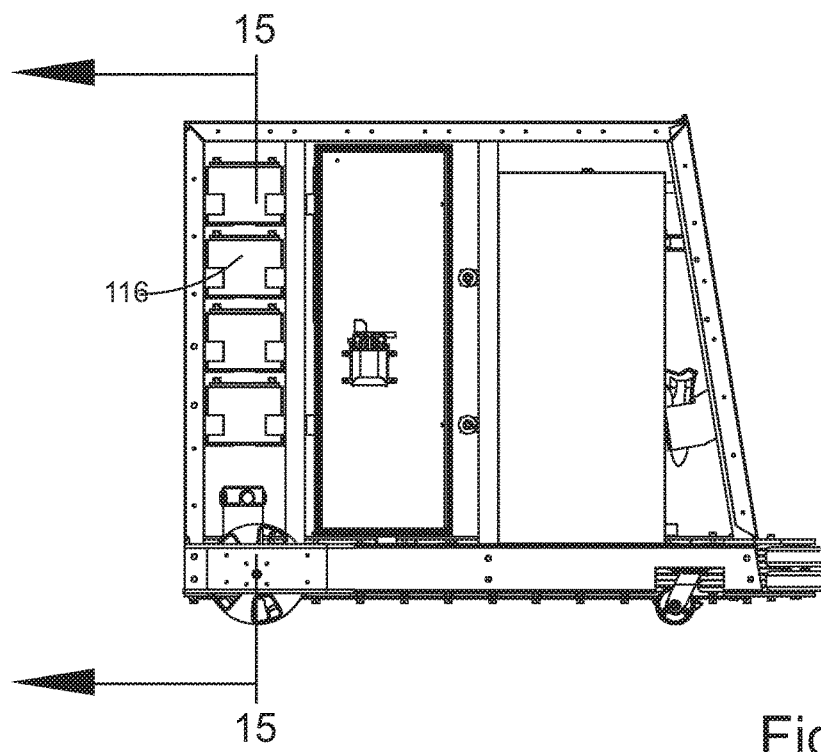
FIG. 16 is a side view showing the cross-section.

FIG. 16 shows the cross-section of FIG. 15 which shows the second battery stack 116 mounted symmetrically to the first battery stack. The first and second battery stack are preferably symmetrical in size and mass with one battery stack on the left and one battery stack on the right to balance each other out.

Figure 17:
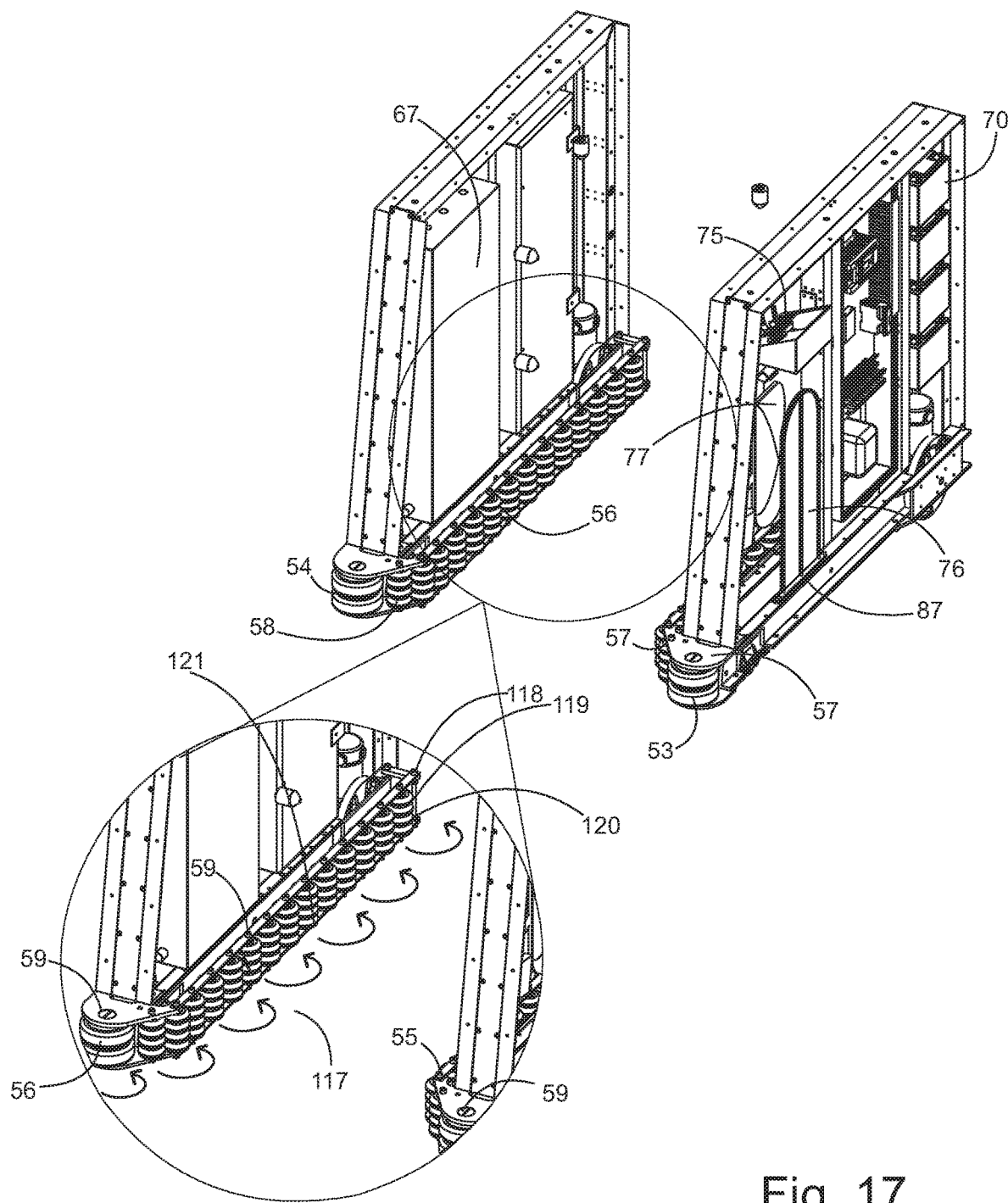
FIG. 17 is a detailed view of the roller stack units.

As seen in FIG. 17, the left front roller 53 and the right front roller 54 align the shopping carts so that the left and right sides of the shopping carts pass along the left roller array 55, and the right roller array 56. The left roller frame 57 is generally symmetrical to the right roller frame 58 and retains rows of roller axles 59 such as fifteen roller axles. The roller direction 117 of the top roller roll 118, the middle roller row 119, and the bottom roller row 120 are synchronized so that all of the roller stack units 121 cooperate to form a horizontally mounted conveyor.

The first fluid tank 67 is vertically oriented and placed between the struts. Similarly, the first battery stack 70 is vertically oriented and placed between vertical struts. The area between struts provides a cabinet cavity for stowing the swivel manual control 75, swivel platform 76, and swivel back rest 77.

Figure 18:
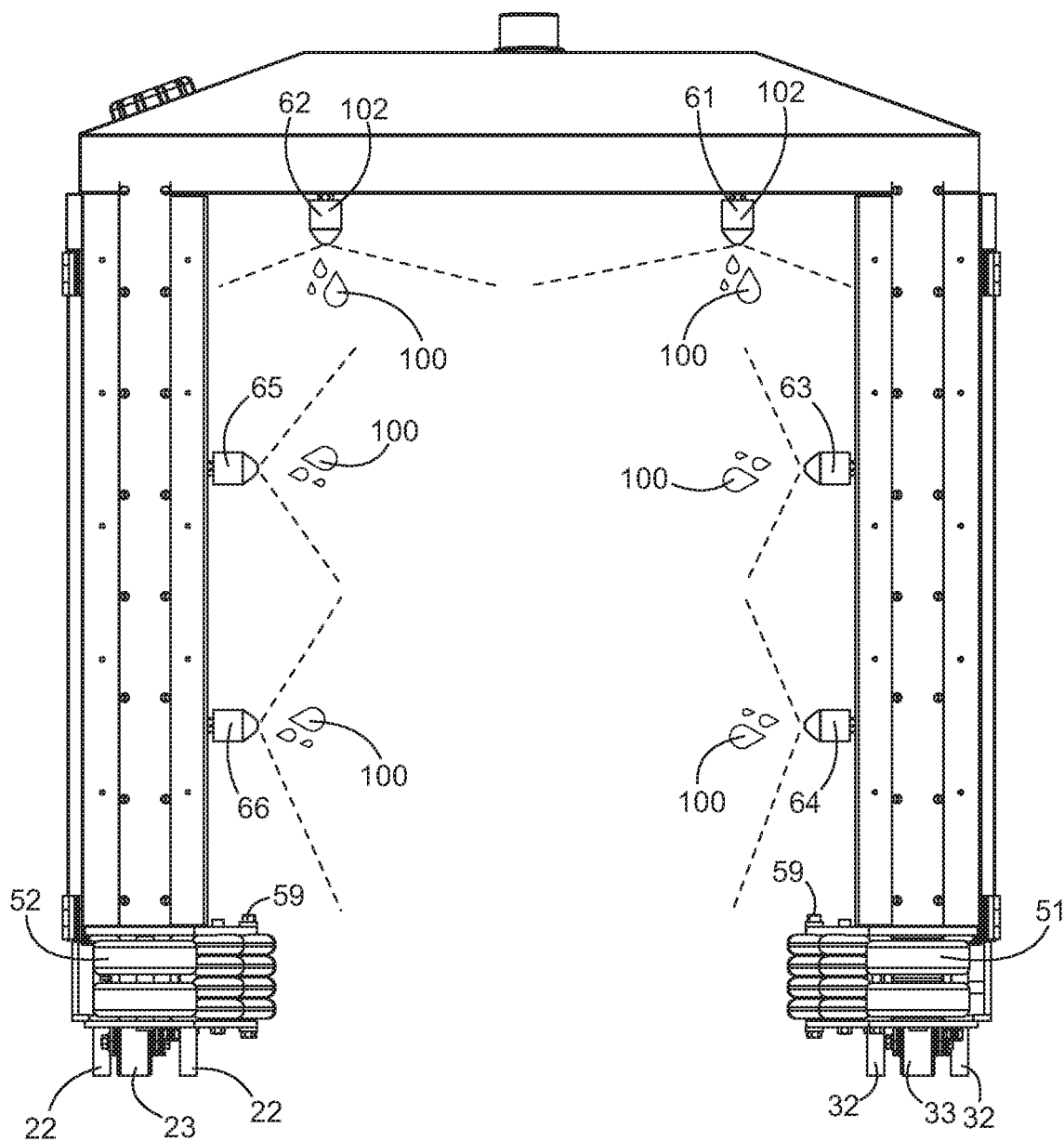
FIG. 18 is a front view diagram showing the spray configuration.

As seen in FIG. 18, from a front plan view, the right front wheel 22 is seen as between the two sections of the right rear wheel 23. The right front wheel 22 and the right rear wheel 23 are positioned underneath the right wall 17 and aligned with each other. Similarly, from a front plan view, the left rear wheel 32 appears between the two sections of the left front wheel 33 because the front and rear wheels are aligned with each other underneath the left wall 16. The tapered portion of the left roller assembly 51 and the tapered portion of the right roller assembly 52 are mounted near the roller axle 59 so that the front wheel 33 can stabilize the tapered portion of the left roller assembly and the tapered portion of the right roller assembly.

Fluid flow 100 is sprayed from fluid nozzles 102. The fluid nozzles 102 include a top left nozzle 61, a top right nozzle 62, an upper left nozzle 63, a lower left nozzle 64, an upper right nozzle 65, and a lower right nozzle 66. Each of the fluid nozzles 102 can be adjusted for different spray patterns according to the needs of the user. The fluid nozzles 102 can be adjusted manually by rotating the nozzle head and could provide a wide spray, a fine mist or a stream, for example.

Figure 19:
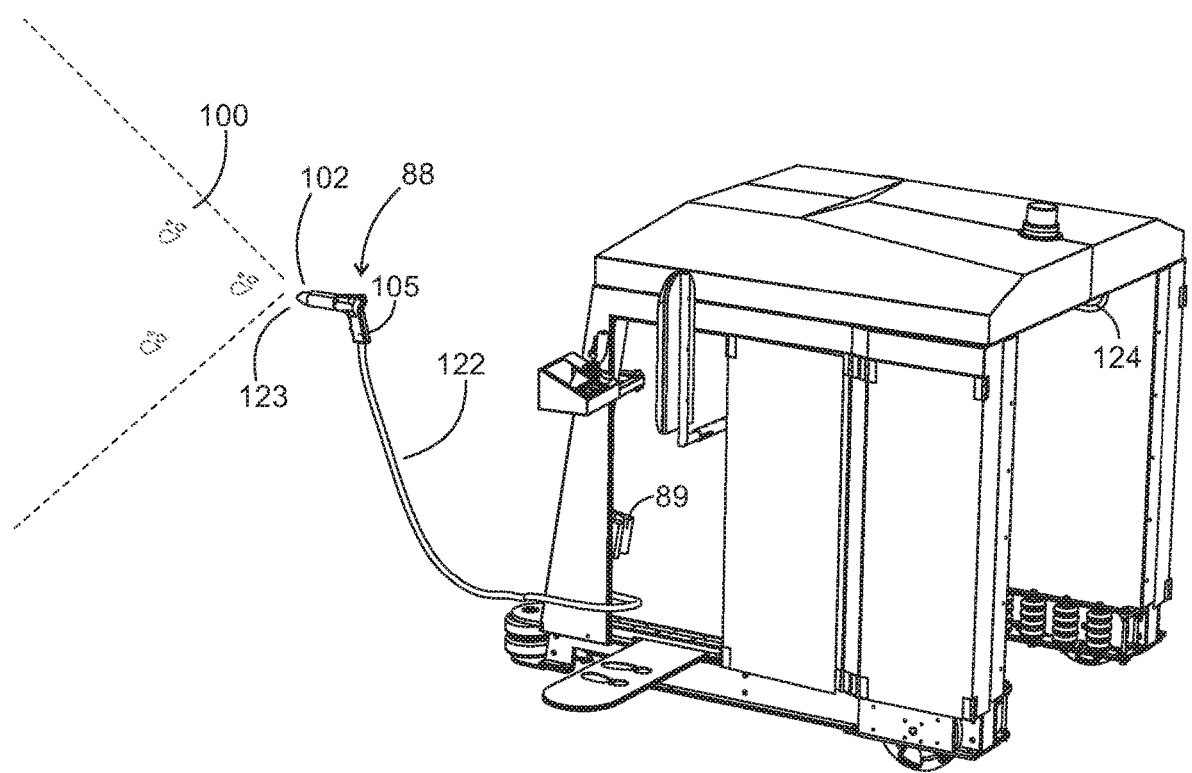
FIG. 19 is a diagram showing use of the sprayer wand.

As seen in FIG. 19, the sprayer gun 88 can be upholstered from the sprayer gun support 89. A fluid flow 100 passes through the hose 122 and exits the fluid nozzle 102. Optionally the fluid sensor 105 can provide fluid sensor data for the client which can synchronize to the server.

The invention claimed is:

1. A method of sanitizing articles using a moving tunnel sanitizer comprising the steps of:
   a. forming a frame with a tunnel and a tunnel opening through the frame;
   b. forming a right wall supporting a right side of the frame;
   c. forming a left wall supporting a left side of the frame;
   d. configuring a right front wheel and a right rear wheel supporting the right wall;
   e. configuring a left front wheel and a left rear wheel supporting the left wall;
   f. configuring a top member, wherein the top member makes a rigid connection between the right wall to the left wall;
   g. configuring nozzles mounted on the tunnel, wherein the nozzles are mounted on the right wall, and the left wall;
   h. installing a fluid tank storing a sanitizing fluid, wherein the fluid tank is connected to the nozzles;
   i. installing a left motor and a right motor, wherein the left motor drives either the front left wheel or the rear left wheel, and wherein the right motor drives the front right wheel or the rear right wheel; and
   j. installing a battery providing electrical power to the left motor and the right motor.

2. The method of sanitizing articles using a moving tunnel sanitizer of claim 1, further including the step of: forming a left front frame rib formed on the left wall of the frame at a left front edge and a right front frame rib formed on the right wall of the frame at a right front edge.

3. The method of sanitizing articles using a moving tunnel sanitizer of claim 1, further including the step of: mounting a right tunnel panel on the right wall, and mounting a left tunnel panel on the left wall.

4. The method of sanitizing articles using a moving tunnel sanitizer of claim 3, further including the step of securing the right tunnel panel with a right tunnel panel overlap connecting to the right front frame rib on the right wall, and further including the step of securing the left tunnel panel with a left tunnel panel overlap connecting to the left front frame rib on the left wall.

5. The method of sanitizing articles using a moving tunnel sanitizer of claim 1, further including the step of forming the top member with a top member frame sandwiched between a top panel frame cover below the top panel frame, and a top panel above the top panel frame, and further including the step of connecting the top panel frame to the right wall and the left wall.

6. The method of sanitizing articles using a moving tunnel sanitizer of claim 1, further including the step of mounting nozzles on the top member facing downward, namely a top right nozzle and a top left nozzle, mounting the nozzles on the right wall which include an upper right nozzle and a lower right nozzle, and mounting the nozzles mounted on the left wall which include an upper left nozzle and a lower left nozzle, further including an electrostatic charge wire with a voltage of at least 10,000 volts mounted to each nozzle.

7. The method of sanitizing articles using a moving tunnel sanitizer of claim 1, further including the step of installing a swivel platform formed on a side of the right wall or the left wall; and configuring the swivel platform to rotate between a swivel platform stowed position and a swivel platform deployed position, and further configuring a swivel manual control to include a CPU and data storage and a joystick.

8. The method of sanitizing articles using a moving tunnel sanitizer of claim 1, further including the step of installing a front camera and a rear camera in connection with a client; and further including the step of connecting a client to the front camera and the rear camera, and further including the step of wirelessly connecting the client through a mobile wireless transceiver to a base station wireless transceiver, and further including the step of configuring the base station wireless transceiver to connect to a gateway, and further configuring the router to connect to a wide area network to connect to a server.

* * * * *